(12) United States Patent
Krus et al.

(10) Patent No.: US 11,617,709 B2
(45) Date of Patent: Apr. 4, 2023

(54) METHYLENE BIS-BENZOTRIAZOLYL TETRAMETHYLBUTYLPHENOL FOR FABRIC STAINING REDUCTION

(71) Applicant: BASF SE, Ludwigshafen am Rhein (DE)

(72) Inventors: Stanislaw Krus, Grenzach-Wyhlen (DE); Marcel Schnyder, Birsfelden (CH)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/282,934

(22) PCT Filed: Oct. 2, 2019

(86) PCT No.: PCT/EP2019/076714
§ 371 (c)(1),
(2) Date: Apr. 5, 2021

(87) PCT Pub. No.: WO2020/070194
PCT Pub. Date: Apr. 9, 2020

(65) Prior Publication Data
US 2021/0386641 A1 Dec. 16, 2021

(30) Foreign Application Priority Data
Oct. 5, 2018 (EP) ..................... 18198901

(51) Int. Cl.
| | | |
|---|---|---|
| *A61K 8/49* | (2006.01) | |
| *A61Q 17/04* | (2006.01) | |
| *A61K 8/27* | (2006.01) | |
| *A61K 8/29* | (2006.01) | |

(52) U.S. Cl.
CPC ............ *A61K 8/496* (2013.01); *A61K 8/4966* (2013.01); *A61Q 17/04* (2013.01); *A61K 8/27* (2013.01); *A61K 8/29* (2013.01); *A61K 2800/5922* (2013.01)

(58) Field of Classification Search
None
See application file for complete search history.

(56) References Cited

U.S. PATENT DOCUMENTS

2014/0328777 A1 11/2014 Mendrok-Edinger
2019/0274939 A1* 9/2019 Floesser-Mueller ... A61K 8/365

FOREIGN PATENT DOCUMENTS

| AU | 2018200455 A1 * | 8/2018 | ............... A61K 8/29 |
|---|---|---|---|
| DE | 102014207916 A1 | 10/2015 | |
| DE | 102014207919 A1 | 10/2015 | |
| DE | 102014207924 A1 | 10/2015 | |
| DE | 102014207935 A1 | 10/2015 | |
| EP | 2939710 A1 | 11/2015 | |
| EP | 3150189 A1 | 4/2017 | |
| EP | 3150190 A1 | 4/2017 | |
| EP | 3150258 A1 | 4/2017 | |
| EP | 3153151 A1 | 4/2017 | |
| EP | 3354253 A2 | 8/2018 | |
| WO | 2010/098099 A1 | 9/2010 | |
| WO | 2016/012586 A1 | 1/2016 | |

OTHER PUBLICATIONS

International Search Report and Written Opinion received for PCT Patent Application No. PCT/EP2019/076714, dated Jan. 2, 2020, 10 pages.

* cited by examiner

*Primary Examiner* — Nannette Holloman
(74) *Attorney, Agent, or Firm* — Faegre Drinker Biddle & Reath LLP (57) ABSTRACT

The present invention relates to the use of methylene bis-benzotriazolyl tetramethylbutylphenol, optionally in combination with tris-biphenyl triazine, to reduce fabric staining of a sunscreen or daily care composition, wherein the sunscreen or daily care composition comprises (i) at least one particulate UV-f liter; and/or (ii) at least one oil soluble UV-A filter, wherein the at least one oil soluble UV-A filter is present in an amount of at most 3% by weight, based on the total weight of the sunscreen or daily care composition; and/or (iii) at least one water soluble UV filter. Furthermore, the present invention relates to the use of methylene bis-benzotriazolyl tetramethylbutylphenol, optionally in combination with tris-biphenyl triazine, to facilitate the washability of such sunscreen or daily care compositions from textiles.

20 Claims, 2 Drawing Sheets

METHYLENE BIS-BENZOTRIAZOLYL TETRAMETHYLBUTYLPHENOL FOR FABRIC STAINING REDUCTION

CROSS-REFERENCE TO RELATED APPLICATIONS

This application is a national stage application (under 35 U.S.C. § 371) of PCT/EP2019/076714, filed Oct. 2, 2019, which claims benefit of European Application No. 18198901.3, filed Oct. 5, 2018, both of which are incorporated herein by reference in their entirety.

The present invention relates to the use of methylene bis-benzotriazolyl tetramethylbutylphenol, optionally in combination with tris-biphenyl triazine, to reduce fabric staining of a sunscreen or daily care composition, wherein the sunscreen or daily care composition further comprises (i) at least one particulate UV-filter; and/or (ii) at least one oil soluble UV-A filter, wherein the at least one oil soluble UV-A filter is present in an amount of at most 3% by weight, based on the total weight of the sunscreen or daily care composition; and/or (iii) at least one water soluble UV filter. Furthermore, the present invention relates to the use of methylene bis-benzotriazolyl tetramethylbutylphenol, optionally in combination with tris-biphenyl triazine, to facilitate the washability of such sunscreen or daily care compositions from textiles.

UV radiation causes harmful effects on the human skin. Beside the acute effect of sunburn of the skin, UV radiation is also known to increase the risk of skin cancer. Furthermore, long time exposure to UV-A and UV-B light can cause phototoxic and photoallergenic reactions on the skin and can accelerate skin aging.

To protect the human skin from UV radiation, various sun protecting UV filters (also referred to as UV absorbers) exist including UV-A filter, UV-B filter and broadband filters. These filters are added to sunscreen or cosmetic compositions. The UV filters are either organic or inorganic compounds, which have a high absorption efficacy in the UV-light range. In general, UV light can be divided into UV-A radiation and UV-B radiation. Depending on the position of the absorption maxima, UV-filters are divided into UV-A and UV-B filters. In case an UV-filter absorbs both, UV-A and UV-B light, it is referred to as a broadband absorber.

Since 2006, the EU commission has recommended that all sunscreen or cosmetic compositions should have an UV-A protection factor, which is at least one third of the labelled sun protection factor (SPF), wherein the sun protection factor refers mainly to the UV-B protection.

However, the use of UV-A filters and broadband filters in sunscreen or cosmetic compositions has certain disadvantages. In particular, sunscreen or cosmetic compositions can adhere on fabrics or textiles and cause fabric staining. In view of the low solubility of the filters, the resulting stains are hard to remove during washing of the fabrics.

Accordingly, it is desired to reduce fabric staining and/or facilitate the washability of sunscreen compositions from textiles without reducing the UV-A protection.

DE 10 2014 207 919 A1 discloses sunscreen compositions with reduced fabric staining comprising bis-ethylhexyloxyphenol methoxyphenyl triazine in combination with certain chelating agents.

DE 10 2014 207 916 A1 discloses sunscreen compositions with reduced fabric staining comprising butyl methoxydibenzoylmethane in combination with certain chelating agents.

In contrast, DE 10 2014 207 935 A1 is directed to sunscreen compositions in general, which show in combination with chelating agents less fabric staining.

DE 10 2014 207 924 A1 the UV-filter diethylamino hydroxybenzoyl hexyl benzoate in combination with certain chelating agents in sunscreen composition for reduced fabric staining.

EP 2 939 710 A1 discloses a method to reduce substantivity of cloth staining caused by sunscreens, whereby the focus is on cosmetic and/or pharmaceutical preparations comprising disodium phenyl benzimidazole tetrasulfonic acid and/or its salts.

EP 3 150 190 A1 discloses sunscreen compositions for reduced fabric staining comprising pirocton and or salts thereof.

EP 3 153 151 A1 is directed to sunscreen compositions which show reduced fabric staining, whereby the sunscreen composition comprises tert-butyl-methoxydibenzoylmethane and at least two additives.

EP 3 150 258 A1 discloses sunscreen compositions comprising bis-ethylhexyloxyphenol methoxyphenyl triazine and pirocton for reduced fabric staining.

EP 3 150 189 is directed to sunscreen compositions comprising diethylamino hydroxybenzoyl hexyl benzoate in combination with pirocton to reduce fabric staining.

EP 3 354 253 A2 discloses the use of diethylamino hydroxybenzoyl hexyl benzoate for the reduction of fabric staining of a cosmetic composition.

However, there remains a need for sunscreen compositions, which are further improved regarding the problem of fabric staining and the washability from textiles without reducing the UV-A protection.

Therefore, it has been an object of the present invention to provide an UV filter providing UV-A protection, which is suitable for use in sunscreen compositions in order to reduce fabric staining and/or to facilitate the washability of sunscreen compositions from textiles.

It has surprisingly been found that this object can be achieved by the use of 2,2'-methylene bis[6-(2H-benzotriazol-2-yl)-4-(1,1,3,3-tetramethylbutyl)phenol] (INCI methylene bis-benzotriazolyltetramethylbutylphenol), optionally in combination with 2,4,6-tris(biphenyl-4-yl)-1,3,5-triazine (INCI tris-biphenyltriazine), in sunscreen or daily care compositions, wherein the sunscreen or daily care compositions further comprise (i) at least one particulate UV-filter; and/or
(ii) at least one oil soluble UV-A filter, wherein the at least one oil soluble UV-A filter is present in an amount of at most 3% by weight, based on the total weight of the sunscreen or daily care composition; and/or
(iii) at least one water soluble UV filter.

In particular, the inventors of the present application found out that by using methylene bis-benzotriazolyl tetramethylbutylphenol in the above defined sunscreen compositions fabric staining of the sunscreen compositions can be reduced and the washability of the stains from textiles can be facilitated. Nevertheless, not only good UV-B protection, but also god UV-A protection can be achieved. This advantages of the present invention may be attributed to the fact that methylene bis-benzotriazolyl tetramethylbutylphenol (MBBT) is a particulate organic UV filter, which provides UV-B and UV-A protection, can be used to replace oil soluble UV-A filters to a large extent or entirely, which is advantageous as oil soluble UV-A filters are often responsible for fabric staining problems, but required in order to provide sufficient UV-A protection. Similarly, also tris-biphenyl triazine (TBPT) is a particulate organic UV filter being advantageous regarding fabric staining problems. Furthermore, while providing protection in the UV-B and UV-AII range, it may have a boosting effect for the protection in the UV-AI range.

Thus, according to one embodiment, the present invention relates to the use of 2,2'-methylene bis[6-(2H-benzotriazol-2-yl)-4-(1,1,3,3-tetramethylbutyl)phenol] (INCI methylene bis-benzotriazolyltetramethylbutylphenol), optionally in combination with 2,4,6-tris(biphenyl-4-yl)-1,3,5-triazine (INCI tris-biphenyl triazine), to reduce fabric staining of a sunscreen or daily care composition, wherein the sunscreen or daily care composition further comprises
(i) at least one particulate UV-filter; and/or
(ii) at least one oil soluble UV-A filter, wherein the at least one oil soluble UV-A filter is present in an amount of at most 3% by weight, based on the total weight of the sunscreen or daily care composition; and/or
(iii) at least one water soluble UV filter.

In another embodiment, the present invention relates to the use of 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), to facilitate the washability of a sunscreen or daily care composition from textiles, wherein the sunscreen or daily care composition further comprises
(i) at least one particulate UV filter; and/or
(ii) at least one oil soluble UV-A filter, wherein the at least one oil soluble UV-A filter is present in an amount of at most 3% by weight, based on the total weight of the sunscreen or daily care composition; and/or
(iii) at least one water soluble UV filter.

In a preferred embodiment of said uses, the at least one particulate UV filter is an organic particulate UV filter, an inorganic particulate UV filter, or a combination thereof.

In a more preferred embodiment, the at least one organic particulate UV-filter is selected from the group consisting of 1,1'-(1,4-piperazinediyl)bis[1-[2-[4-(diethylamino)-2-hydroxybenzoyl]phenyl]-methanone (INCI bis-(diethylamino-hydroxybenzoyl benzoyl) piperazine), 5,6,5',6'-tetraphenyl-3-3'-(1,4-phenylene)bis(1,2,4-triazine) (INCI phenylene bis-diphenyltriazine), and combinations thereof.

In another more preferred embodiment, the at least one inorganic particulate UV-filter is selected from the group consisting of titanium dioxide, zinc oxide, and combinations thereof.

In another preferred embodiment of said use, the sunscreen or daily care composition comprises the at least one particulate UV filter in an amount of from 0.1 to 10% by weight, preferably in an amount of from 0.5 to 7% by weight, based on the total weight of the sunscreen or daily care composition.

In another preferred embodiment of said uses, the sunscreen or daily care composition comprises 2,2'-methylene bis[6-(2H-benzotriazol-2-yl)-4-(1,1,3,3-tetramethylbutyl) phenol] (INCI methylene bis-benzotriazolyl tetramethylbutylphenol), optionally in combination with 2,4,6-tris(biphenyl-4-yl)-1,3,5-triazine (INCI tris-biphenyl triazine), and at least one particulate UV filter, but no further oil soluble or water soluble UV filter. In this connection, it is a more preferred embodiment that the sunscreen or daily care composition comprises an overall amount of from 2 to 30% by weight, preferably an overall amount of from 5 to 20% by weight, based on the total weight of the sunscreen or daily care composition, of particulate UV filters.

In another preferred embodiment of said uses, the at least one oil soluble UV-A filter is selected from the group consisting of hexyl 2-[4-(diethylamino)-2-hydroxybenzoyl] benzoate (INCI diethylamino hydroxybenzoyl hexyl benzoate), 1-(4-(1,1-dimethylethyl)phenyl)-3-(4-methoxyphenyl) propane-1,3-dione (INCI butyl methoxydibenzoylmethane), 2-(2H-benzotriazol-2-yl)-6-[(2-ethylhexyloxy)methyl]-4-methylphenol, 2-(2H-benzotriazol-2-yl)-4-methyl-6-[2-methyl-3-[1,3,3,3-tetramethyl-1-[(trimethylsilyl)oxy]-1-disiloxanyl]propyl]phenol (INCI drometrizole trisiloxane), and combinations thereof. Preferably, the oil soluble UV-A filter is hexyl 2-[4-(diethylamino)-2-hydroxybenzoyl]benzoate (INCI diethylamino hydroxybenzoyl hexyl benzoate) or 1-(4-(1,1-dimethylethyl)phenyl)-3-(4-methoxyphenyl) propane-1,3-dione (INCI butyl methoxydibenzoylmethane).

In another preferred embodiment of said uses, the at least one water soluble UV filter is selected from the group consisting of [(3Z)-3-[[4-[(Z)-[7,7-dimethyl-2-oxo-1-(sulfomethyl)-3-bicyclo[2.2.1]heptanylidene]methyl]phenyl] methylidene]-7,7-dimethyl-2-oxo-1-bicyclo[2.2.1]heptanyl] methanesulfonic acid (INCI terephthalylidene dicamphor sulfonic acid), 2-phenyl-1H-benzimidazole-5-sulfonic acid (INCI phenylbenzimidazole sulfonic acid), disodium phenyl dibenzimidazole tetrasulfonate, and combinations thereof.

In another preferred embodiment of said uses, the sunscreen or daily care composition comprises the at least one water soluble UV filter in an amount of from 0.1 to 6% by weight, preferably in an amount of from 0.5 to 3% by weight, based on the total weight of the sunscreen or daily care composition.

In another preferred embodiment of said uses, the sunscreen or daily care composition comprises the 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 0.1 to 10% by weight, preferably in an amount of from 0.5 to 5% by weight, based on the total weight of the sunscreen or daily care composition.

In another preferred embodiment of said uses, the sunscreen or daily care composition comprises the 2,4,6-tris (biphenyl-4-yl)-1,3,5-triazine (INCI tris-biphenyl triazine), if present, in an amount of from 0.1 to 10% by weight, preferably from 0.5 to 7% by weight, based on the total weight of the sunscreen composition or daily care composition.

In another preferred embodiment of said uses, the sunscreen or daily care composition further comprises at least one UV-B filter, preferably at least one oil soluble UV-B filter. In another preferred embodiment of said uses, the at least one further UV-B filter is selected from the group consisting of 4,4',4"-(1,3,5-triazine-2,4,6-triyltriimino)tris-benzoic acid-tris(2-ethylhexyl)ester (INCI ethylhexyl triazone), (RS)-2-ethylhexyl-2-hydroxybenzoate (INCI ethylhexyl salicylate), 3,3,5-trimethyl-cyclohexyl salicylate (homosalate), 2-ethylhexyl 2-cyano-3,3-diphenyl-2-propenoate (INCI octocrylene), (RS)-2-ethylhexyl-(2E)-3-(4-methoxyphenyl)prop-2-enoate (INCI ethylhexyl methoxycinnamate), malonate derivatives such as dimethicone diethyl benzalmalonate, diethylhexyl butamido triazone, and combinations thereof.

In yet another preferred embodiment of said uses, the sunscreen or daily care composition further comprises at least one oil soluble broad spectrum UV filter, wherein the at least one oil soluble broad spectrum UV filer is preferably 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine).

Furthermore, the present invention relates to the use of 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), to reduce fabric staining of a sunscreen or daily care composition and/or to facilitate the washability of a sunscreen or daily care composition from textiles, wherein the sunscreen or daily care composition further comprises     at least one UV-B filter, which is diethylhexyl butamido triazone; and     at least one oil soluble broad spectrum UV filer, which is 2,4-bis-{[4-(2-ethyl-hexyloxy)-2-hydroxy]-phenyl}-6-(4-methoxyphenyl)-1,3,5-triazine (I NCI bis-ethylhexyloxyphenol methoxyphenyl triazine).

In another aspect, the present invention relates to a method to reduce fabric staining of a sunscreen or daily care composition, wherein the method comprises adding 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), to the sunscreen composition, wherein the sunscreen or daily care composition further comprises (i) at least one particulate UV-filter; and/or (ii) at least one oil soluble UV-A filter, wherein the at least one oil soluble UV-A filter is present in an amount of at most 3% by weight, based on the total weight of the sunscreen or daily care composition; and/or (iii) at least one water soluble UV filter.

In another aspect, the present invention relates to a method to facilitate the washability of a sunscreen or daily care composition from textiles, wherein the method comprises adding 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), to the sunscreen or daily care composition, wherein the sunscreen or daily care composition further comprises (i) at least one particulate UV-filter; and/or (ii) at least one oil soluble UV-A filter, wherein the at least one oil soluble UV-A filter is present in an amount of at most 3% by weight, based on the total weight of the sunscreen or daily care composition; and/or (iii) at least one water soluble UV filter.

In a preferred embodiment of said methods, the at least one particulate UV filter is an organic particulate UV filter, an inorganic particulate UV filter, or a combination thereof.

In a more preferred embodiment, the at least one organic particulate UV-filter is selected from the group consisting of 1,1'-(1,4-piperazinediyl)bis[1-[2-[4-(diethylamino)-2-hydroxybenzoyl]phenyl]-methanone (INCI bis-(diethylamino-hydroxybenzoyl benzoyl) piperazine), 5,6,5',6'-tetraphenyl-3-3'-(1,4-phenylene)bis(1,2,4-triazine) (INCI phenylene bis-diphenyltriazine), and combinations thereof.

In another more preferred embodiment, the at least one inorganic particulate UV-filter is selected from the group consisting of titanium dioxide, zinc oxide, and combinations thereof.

In another preferred embodiment of said methods, the sunscreen or daily care composition comprises the at least one particulate UV filter in an amount of from 0.1 to 10% by weight, preferably in an amount of from 0.5 to 7% by weight, based on the total weight of the sunscreen or daily care composition.

In another preferred embodiment of said methods, the sunscreen composition comprises 2,2'-methylene bis[6-(2H-benzotriazol-2-yl)-4-(1,1,3,3-tetramethylbutyl)phenol] (INCI methylene bis-benzotriazolyltetramethylbutylphenol), optionally in combination with 2,4,6-tris(biphenyl-4-yl)-1,3,5-triazine (INCI tris-biphenyl triazine), and at least one particulate UV filter, but no further oil soluble or water soluble UV filter. In this connection, it is a more preferred embodiment that the sunscreen or daily care composition comprises an overall amount of from 2 to 30% by weight, preferably an overall amount of from 5 to 20% by weight, based on the total weight of the sunscreen or daily care composition, of particulate UV filters.

In another preferred embodiment of said methods, the at least one oil soluble UV-A filter is selected from the group consisting of hexyl 2-[4-(diethylamino)-2-hydroxybenzoyl]benzoate (INCI diethylamino hydroxybenzoyl hexyl benzoate), 1-(4-(1,1-dimethylethyl)phenyl)-3-(4-methoxyphenyl)propane-1,3-dione (INCI butyl methoxydibenzoylmethane), 2-(2H-benzotriazol-2-yl)-6-[(2-ethylhexyloxy)methyl]-4-methylphenol, 2-(2H-benzotriazol-2-yl)-4-methyl-6-[2-methyl-3-[1,3,3,3-tetramethyl-1-[(trimethylsilyl)oxy]-1-disiloxanyl]propyl]phenol (INCI drometrizole trisiloxane), and combinations thereof. Preferably, the oil soluble UV-A filter is hexyl 2-[4-(diethylamino)-2-hydroxybenzoyl]benzoate (INCI diethylamino hydroxybenzoyl hexyl benzoate) or 1-(4-(1,1-dimethylethyl)phenyl)-3-(4-methoxyphenyl)propane-1,3-dione (INCI butyl methoxydibenzoylmethane).

In another preferred embodiment of said methods, the at least one water soluble UV filter is selected from the group consisting of [(3Z)-3-[[4-[(Z)-[7,7-dimethyl-2-oxo-1-(sulfomethyl)-3-bicyclo[2.2.1]heptanylidene]methyl]phenyl]methylidene]-7,7-dimethyl-2-oxo-1-bicyclo[2.2.1]heptanyl]methanesulfonic acid (INCI terephthalylidene dicamphor sulfonic acid), 2-phenyl-1H-benzimidazole-5-sulfonic acid (INCI phenylbenzimidazole sulfonic acid), disodium phenyl dibenzimidazole tetrasulfonate, and combinations thereof.

In another preferred embodiment of said methods, the sunscreen or daily care composition comprises the at least one water soluble UV filter in an amount of from 0.1 to 6% by weight, preferably in an amount of from 0.5 to 3% by weight, based on the total weight of the sunscreen or daily care composition.

In another preferred embodiment of said methods, the sunscreen or daily care composition comprises the 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 0.1 to 10% by weight, preferably in an amount of from 0.5 to 5% by weight, based on the total weight of the sunscreen or daily care composition.

In another preferred embodiment of said uses, the sunscreen or daily care composition comprises the 2,4,6-tris(biphenyl-4-yl)-1,3,5-triazine (INCI tris-biphenyl triazine), if present, in an amount of from 0.1 to 10% by weight, preferably from 0.5 to 7% by weight, based on the total weight of the sunscreen composition or daily care composition.

In another preferred embodiment of said methods, the sunscreen or daily care composition further comprises at least one UV-B filter, preferably at least one oil soluble UV-B filter.

In a more preferred embodiment of said methods, the at least one further UV-B filter is selected from the group consisting of 4,4',4''-(1,3,5-triazine-2,4,6-triyltriimino)tris-benzoic acid-tris(2-ethylhexyl)ester (INCI ethylhexyl triazone), (RS)-2-ethylhexyl-2-hydroxybenzoate (INCI ethylhexyl salicylate), 3,3,5-trimethyl-cyclohexyl salicylate (homosalate), 2-ethylhexyl 2-cyano-3,3-diphenyl-2-propenoate (INCI octocrylene), (RS)-2-ethylhexyl-(2E)-3-(4- methoxyphenyl)prop-2-enoate (INCI ethylhexyl methoxycinnamate), malonate derivatives such as dimethicone diethyl benzalmalonate, diethylhexyl butamido triazone, and combinations thereof.

In yet another preferred embodiment of said methods, the sunscreen or daily care composition further comprises at least one oil soluble broad spectrum UV filter, wherein the at least one oil soluble broad spectrum UV filer is preferably 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine).

Furthermore, the present invention relates to a method to reduce fabric staining and/or to facilitate the washability from textiles of a sunscreen or daily care composition, wherein the method comprises adding 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), wherein the sunscreen or daily care composition further comprises
- at least one UV-B filter, which is diethylhexyl butamido triazone; and
- at least one oil soluble broad spectrum UV filer, which is 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine).

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention, the term "consisting of" is considered to be a preferred embodiment of the term "comprising of". If hereinafter a group is defined to comprise at least a certain number of embodiments, this is meant to also encompass a group, which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The term "sunscreen composition" refers to any topical product, which reflects or absorbs certain parts of UV radiation. Thus, the term "sunscreen composition" is to be understood as not only including sunscreen compositions, but also any cosmetic compositions that provide UV protection. The term "topical product" refers to a product that is applied to the skin and can refer, e.g., to sprays, lotions, creams, oils, or gels. The sunscreen composition may comprise one or more active agents, e.g., organic or inorganic UV filters, as well as other ingredients or additives, e.g., emulsifiers, emollients, viscosity regulators, stabilizers, preservatives, or fragrances.

The term "daily care composition" refers to any topical product, which reflects or absorbs certain parts of UV radiation and is used as an everyday care product for the human body, e.g., for face, body or hair. The daily care composition may comprise one or more active agents, e.g., organic or inorganic UV filters, as well as other ingredients or additives, e.g., emulsifiers, emollients, viscosity regulators, stabilizers, preservatives, or fragrances.

The term "fabric staining" as used herein refers to the observation that sunscreen compositions, in particular those providing good UV-A protection, leave yellow stains on textiles. This is undesired because the sunscreen composition is often in contact with textiles during or after the application to the human skin, so that stains will be observed on the textiles. Staining of fabrics can be measured by the L*a*b method as outlined in detail below.

The term "washability" as used herein describes to which extent stains on textiles caused by sunscreen compositions can be removed from the textile after a certain number of washing cycles. In order to assess the washability, fabric staining is measured before and after one or more washing cycles. A washing cycle is carried out at a temperature of from 30° C. to 50° C. with a commercially available liquid washing gel. Typically, the difference regarding fabric staining after 1 to 3 washing cycles is determined.

The term "UV-filter" as used herein refers to organic or inorganic compounds, which can absorb and/or reflect UV radiation caused by sunlight. UV-filter can be classified based on their UV protection curve as UV-A, UV-B or broadband filters. Broadband UV filters may also be referred to as broad spectrum UV filters. A preferred broad spectrum UV filter as used herein is bis-ethylhexyloxyphenol methoxyphenyl triazine (BEMT).

Furthermore, UV filters can be classified according to their solubility behavior, e.g., water soluble UV filters, oil soluble UV filters, or particulate UV-filters.

Water soluble UV filters have a solubility in water of at least 2% by weight, preferably at least 3% by weight, more preferably at least 5% by weight.

Oil soluble UV filters have a solubility in common cosmetic oils, such as $C_{12}$-$C_{15}$-alkyl benzoate, dibutyl adipate, diisopropyl sebacate, phenethyl benzoate, or dicaprylyl carbonate of at least 2% by weight, preferably at least 5% by weight, more preferably at least 7% by weight.

The particulate UV filters can be further divided into organic particulate UV filters and inorganic particulate UV filters. While organic particulate UV filters are based on organic compounds, inorganic particulate UV filters are based on inorganic compounds such as titanium dioxide. In the sunscreen composition, particulate UV filters will be present in particulate form, as their solubility is less than 0.01% by weight, preferably less than 0.05% by weight in the sunscreen composition, i.e. in the water and the cosmetic oils contained therein. Preferably, the particulate UV filters have a particle size Dv50 determined by light scattering of less than 2000 nm, preferably less than 1000 nm, wherein Dv50 refers to the particle size value, where half of the population lies below this value, and half of the population lies above this value, i.e. the median value of the particle size volume distribution. If the particles are provided as nanoparticles, the particulate UV filters preferably exhibit a Dv10 in the range of from 50 to 80 nm, a Dv50 in the range of from 75 to 125 nm, and a Dv90 in the range of from 140 to 180 nm. The particle size may be determined in a suspension of the particulate UV filter in water, preferably at a concentration level of 3 mg/L.

2'-methylene bis[6-(2H-benzotriazol-2-yl)-4-(1,1,3,3-tetramethylbutyl)phenol] (INCI methylene bis-benzotriazolyl tetramethylbutylphenol) is a broad spectrum UV filter, which absorbs UV-B light as well as UV-A light. Furthermore, it is a hybrid UV filter, which absorbs UV light as an organic compound, but also scatters some of the light, since it is a particulate UV filter, which is typically present in the form microfine organic particles. The particle size Dv50 determined by light scattering is preferably less than 200 nm, preferably of from 50 to 150 nm. Preferably, the particles exhibit a Dv10 in the range of from 50 to 80 nm, a Dv50 in the range of from 75 to 125 nm, and a Dv90 in the range of from 140 to 180 nm. Methylene-bis-benzotriazolyl tetramethylbutylphenol (also referred to as MBBT) is a UV filter belonging to the group of benzotriazole derivatives. It is sold under the tradename Tinosorb M by BASF.

2,4,6-Tris(biphenyl-4-yl)-1,3,5-triazine (INCI tris-biphenyl triazine), also referred to as TBPT, is a particulate organic UV filter belonging to the group of triazine derivatives. It is sold under the tradename Tinosorb A2B by BASF. It provides protection in the UV-AII and UV-B range with an absorbance maximum at 310 nm. Preferably, the particles exhibit a Dv10 in the range of from 50 to 80 nm, a Dv50 in the range of from 75 to 125 nm, and a Dv90 in the range of from 140 to 180 nm.

Further UV filters are described in detail below.

The term "sun protection factor (SPF)" as used herein indicates how well the skin is protected by a sunscreen composition mainly from UV-B radiation. In particular, the factor indicates how much longer the protected skin may be exposed to the sun without getting a sunburn in comparison to untreated skin. For example, if a sunscreen composition with an SPF of 15 is evenly applied to the skin of a person usually getting a sunburn after 10 minutes in the sun, the sunscreen allows the skilled person to stay in the sun 15 times longer. In other words, SPF 15 means that $\frac{1}{15}$ of the burning UV radiation will reach the skin, assuming sunscreen is applied evenly at a thick dosage of 2 milligrams per square centimeter ($mg/cm^2$).

The term "critical wavelength" is defined as the wavelength at which the area under the UV protection curve (% protection versus wavelength) represents 90% of the total area under the curve in the UV region (290-400 nm). For example, a critical wavelength of 370 nm indicates that the protection of the sunscreen composition is not limited to the wavelengths of UV-B, i.e. wavelengths from 290-320 nm, but extends to 370 nm in such a way that 90% of the total area under the protective curve in the UV region are reached at 370 nm.

The definition of "broadband" protection (also referred to as broad-spectrum or broad protection) is based on the "critical wavelength". For broadband coverage, UV-B and UV-A protection must be provided. According to the US requirements, a critical wavelength of at least 370 nm is required for achieving broad spectrum protection.

Preferred embodiments regarding the uses of 2,2'-methylene bis[6-(2H-benzotriazol-2-yl)-4-(1,1,3,3-tetramethylbutyl)phenol] (INCI methylene bis-benzotriazolyl tetramethylbutylphenol) as well as methods comprising its application according to the present invention are described hereinafter. It is to be understood that the preferred embodiments of the invention are preferred alone or in combination with each other.

As indicated above, the present invention relates in one embodiment to the use of 2,2'-methylene bis[6-(2H-benzotriazol-2-yl)-4-(1,1,3,3-tetramethylbutyl)phenol] (INCI methylene bis-benzotriazolyltetramethylbutylphenol), optionally in combination with 2,4,6-tris(biphenyl-4-yl)-1,3,5-triazine (INCI tris-biphenyl triazine), to reduce fabric staining of a sunscreen or daily care composition, wherein the sunscreen or daily care composition further comprises (i) at least one particulate UV-filter; and/or
(ii) at least one oil soluble UV-A filter, wherein the at least one oil soluble UV-A filter is present in an amount of at most 3% by weight, based on the total weight of the sunscreen or daily care composition; and/or
(iii) at least one water soluble UV filter.

Fabric staining of sunscreen compositions is preferably measured by the so-called L*a*b method mentioned above. With this method, the color difference between two samples can be identified based on numerical values. The advantage of this method is that it is not dependent on the device used for measuring the colors. Instead, the color difference can be determined based on numerical values for different colors. As used herein, the color difference between a sunscreen composition stain on a textile and the textile alone is determined in order to determine fabric staining of a sunscreen composition. Different sunscreen compositions and their fabric staining properties can thus be measured by comparing the color of their stains on a textile with the color of the textile alone. The lower the color difference is, the less fabric staining is observed. Similarly, the color difference between a sunscreen composition stain on a textile after one or more washing cycles and the textile alone can be determined in order to determine a potential reduction of fabric staining after washing, i.e. the washability. The color difference is indicated in absolute color coordinates and can be referred to as Delta Δ. First, the colors of the two samples are measured. Then, the difference can be calculated using the resulting colorimetric values, the CIE L*a*b coordinates. The L*a*b color space, defined by the Commission Internationale de l'Eclairage (CIE), was modeled after a color-opponent theory. This theory states that two colors cannot be red and green at the same time or yellow and blue at the same time. The following formula is used to determine the total color difference between two samples:

$$\Delta E^* = [\Delta L^{*2} + \Delta a^{*2} + \Delta b^{*2}]^{\frac{1}{2}}$$

In this regard, L* indicates lightness, a* is the red/green coordinate, and b* is the yellow/blue coordinate. Delta values for L* (ΔL*), a* (Δa*), and b* (Δb*) can be positive or negative. The total difference, given as ΔE* is always positive.

$\Delta L^*$ ($L^*$sample 1–$L^*$sample 2)=difference in lightness and darkness (+ is lighter, – is darker).

$\Delta a^*$ ($a^*$sample 1–$a^*$sample 2)=difference in red and green (+ is redder, – is greener)

$\Delta b^*$ ($b^*$sample 1–$b^*$sample 2)=difference in yellow and green (+ is yellower, – is greener)

$\Delta E^*$=total color difference.

In order to determine fabric staining according to the present invention, the color of the stain on a textile is compared to the color of the textile alone. Preferably, a white textile is used. In case the stain is only yellow, ΔE*=Δb*, wherein the visibility of the sunscreen composition stain is expressed by Δb*. As the color of a sunscreen composition stain is typically yellow, ΔE* is considered to be identical to Δb* for the purpose of the present invention.

In another embodiment, the present invention relates to the use of 2,2'-methylene bis[6-(2H-benzotriazol-2-yl)-4-(1,1,3,3-tetramethylbutyl)phenol] (INCI methylene bis-benzotriazolyl tetramethylbutylphenol) optionally in combination with 2,4,6-tris(biphenyl-4-yl)-1,3,5-triazine (INCI tris-biphenyl triazine), to facilitate the washability of a sunscreen or daily care composition from textiles, wherein the sunscreen or daily care composition further comprises
  (i) at least one particulate UV filter; and/or
  (ii) at least one oil soluble UV-A filter, wherein the at least one oil soluble UV-A filter is present in an amount of at most 3% by weight, based on the total weight of the sunscreen or daily care composition; and/or
  (iii) at least one water soluble UV filter.

As used herein, the washability refers to the extent to which sunscreen composition stains on textiles can be removed by washing. The washability, i.e. the removability, of a sunscreen composition stain can be determined by determining the color difference of the stain according to the L*a*b* method described above before and after one or more washing cycles.

In connection with the present invention, the following preferred embodiments regarding the sunscreen composition are relevant.

In a preferred embodiment of the present invention, the sunscreen composition has an UV-A protection, which is at least one third of the sun protection factor as defined above. For example, if the sun protection factor of a sunscreen composition is 30 the UV-A protection of the given sunscreen composition has to be at least 10. In another preferred embodiment of the invention, the UV-A protection of the sunscreen composition has to show a critical wavelength of at least 370 nm. In another preferred embodiment of the invention, the sunscreen composition has an UV-A protection, which is at least one third of the sun protection factor as defined above, and also shows a critical wavelength of at least 370 nm.

A skilled person is aware that a sunscreen or daily care composition providing good UV-A protection according to the above criteria requires the presence of at least one UV-A filter. As used herein, 2,2'-methylene bis[6-(2H-benzotriazol-2-yl)-4-(1,1,3,3-tetramethylbutyl)phenol] (INCI methylene bis-benzotriazolyl tetramethylbutylphenol), also referred to as MBBT, serves as broad spectrum UV filter also providing UV-A protection. In connection with the provision of a good UV-A protection, it has surprisingly been found by the inventors of the present invention that by use of MBBT, the use of oil soluble UV-A filters can be reduced significantly or is not required at all, so that the use of MBBT reduces fabric staining and improves the washability of sunscreen and daily care compositions.

In one embodiment, the present invention relates to the use of MBBT, optionally in combination with TBPT, to reduce fabric staining of a sunscreen or daily care composition, wherein the sunscreen or daily care composition further comprises at least one particulate UV filter.

In another embodiment, the present invention relates to the use of MBBT, optionally in combination with TBPT, to reduce fabric staining of a sunscreen or daily care composition, wherein the sunscreen or daily care composition further comprises at least one oil soluble UV-A filter, wherein the at least one oil soluble UV-A filter is present in an amount of at most 3% by weight, based on the total weight of the sunscreen or daily care composition.

In yet another embodiment, the present invention relates to the use of MBBT, optionally in combination with TBPT, to reduce fabric staining of a sunscreen or daily care composition, wherein the sunscreen or daily care composition further comprises at least one water soluble UV filter.

In yet another embodiment, the present invention relates to the use of MBBT, optionally in combination with TBPT, to reduce fabric staining of a sunscreen or daily care composition, wherein the sunscreen or daily care composition further comprises at least one particulate UV-filter; and at least one oil soluble UV-A filter, wherein the at least one oil soluble UV-A filter is present in an amount of at most 3% by weight, based on the total weight of the sunscreen or daily care composition.

In yet another embodiment, the present invention relates to the use of MBBT, optionally in combination with TBPT, to reduce fabric staining of a sunscreen or daily care composition, wherein the sunscreen or daily care composition further comprises at least one oil soluble UV-A filter, wherein the at least one oil soluble UV-A filter is present in an amount of at most 3% by weight, based on the total weight of the sunscreen or daily care composition; and at least one water soluble UV filter.

In yet another embodiment, the present invention relates to the use of MBBT, optionally in combination with TBPT, to reduce fabric staining of a sunscreen or daily care composition, wherein the sunscreen or daily care composition further comprises at least one particulate UV-filter; and at least one water soluble UV filter.

In yet another embodiment, the present invention relates to the use of MBBT, optionally in combination with TBPT, to reduce fabric staining of a sunscreen or daily care composition, wherein the sunscreen or daily care composition further comprises
  (i) at least one particulate UV-filter; and
  (ii) at least one oil soluble UV-A filter, wherein the at least one oil soluble UV-A filter is present in an amount of at most 3% by weight, based on the total weight of the sunscreen or daily care composition; and
  (iii) at least one water soluble UV filter.

If the sunscreen or daily care composition further comprises at least one particulate UV filter, it can be preferred regarding the problem of fabric staining that the sunscreen composition comprises no further oil soluble or water soluble UV filter.

Thus, in one preferred embodiment, the present invention relates to the use of MBBT, optionally in combination with TBPT, to reduce fabric staining of a sunscreen or daily care composition, wherein the sunscreen or daily care composition further comprises at least one particulate UV filter, but no further oil soluble or water soluble UV filter.

In one embodiment, the present invention relates to the use of MBBT, optionally in combination with TBPT, to facilitate the washability of a sunscreen or daily care composition from textiles, wherein the sunscreen or daily care composition further comprises at least one particulate UV filter.

In another embodiment, the present invention relates to the use of MBBT, optionally in combination with TBPT, to facilitate the washability of a sunscreen or daily care composition from textiles, wherein the sunscreen or daily care composition further comprises at least one oil soluble UV-A filter, wherein the at least one oil soluble UV-A filter is present in an amount of at most 3% by weight, based on the total weight of the sunscreen or daily care composition.

In yet another embodiment, the present invention relates to the use of MBBT, optionally in combination with TBPT, to facilitate the washability of a sunscreen or daily care composition from textiles, wherein the sunscreen or daily care composition further comprises at least one water soluble UV filter.

In yet another embodiment, the present invention relates to the use of MBBT, optionally in combination with TBPT, to facilitate the washability of a sunscreen or daily care composition from textiles, wherein the sunscreen or daily care composition further comprises at least one particulate UV-filter; and at least one oil soluble UV-A filter, wherein the at least one oil soluble UV-A filter is present in an amount of at most 3% by weight, based on the total weight of the sunscreen or daily care composition.

In yet another embodiment, the present invention relates to the use of MBBT, optionally in combination with TBPT, to facilitate the washability of a sunscreen or daily care composition from textiles, wherein the sunscreen or daily care composition further comprises at least one oil soluble UV-A filter, wherein the at least one oil soluble UV-A filter is present in an amount of at most 3% by weight, based on the total weight of the sunscreen or daily care composition; and at least one water soluble UV filter.

In yet another embodiment, the present invention relates to the use of MBBT, optionally in combination with TBPT, to facilitate the washability of a sunscreen or daily care composition from textiles, wherein the sunscreen or daily care composition further comprises at least one particulate UV-filter; and at least one water soluble UV filter.

In yet another embodiment, the present invention relates to the use of MBBT, optionally in combination with TBPT, to facilitate the washability of a sunscreen or daily care composition from textiles, wherein the sunscreen or daily care composition further comprises
(i) at least one particulate UV-filter; and
(ii) at least one oil soluble UV-A filter, wherein the at least one oil soluble UV-A filter is present in an amount of at most 3% by weight, based on the total weight of the sunscreen or daily care composition; and
(iii) at least one water soluble UV filter.

If the sunscreen or daily care composition further comprises at least one particulate UV filter, it can be preferred regarding the facilitation of the washability that the sunscreen composition comprises no further oil soluble or water soluble UV filter.

Thus, in one preferred embodiment, the present invention relates to the use of MBBT, optionally in combination with TBPT, to facilitate the washability of a sunscreen or daily care composition from textiles, wherein the sunscreen or daily care composition further comprises at least one particulate UV filter, but no further oil soluble or water soluble UV filter.

In connection with the above embodiments of the invention, "at least one" preferably means from 1 to 3, more preferably 1 or 2.

Further, it is preferred in connection with the above embodiments of the invention that the sunscreen or daily care composition comprises the 2,2'-methylene bis[6-(2H-benzotriazol-2-yl)-4-(1,1,3,3-tetramethylbutyl)phenol] (INCI methylene bis-benzotriazolyl tetramethylbutylphenol), i.e. the MBBT, in an amount of from 0.1 to 10% by weight, preferably in an amount of from 0.5 to 5% by weight, based on the total weight of the sunscreen or daily care composition. These amounts are preferred irrespective of whether MBBT is present in combination with at least one particulate UV filter, at least one oil soluble UV-A filter or at least one water soluble UV filter, or any combination of the foregoing.

Further, it is preferred in connection with the above embodiments of the invention that the sunscreen or daily care composition comprises the 2,4,6-tris(biphenyl-4-yl)-1,3,5-triazine (INCI tris-biphenyl triazine), if present, in an amount of from 0.1 to 10% by weight, preferably from 0.5 to 7% by weight, based on the total weight of the sunscreen composition or daily care composition.

The following preferences regarding the particulate UV filters, the oil soluble UV-filters, and the water soluble UV filters are relevant in connection with the above listed embodiments of the invention.

In a preferred embodiment, the at least one particulate UV filter, which is present in the sunscreen or daily care composition in addition to MBBT, and optionally TBPT, is an organic particulate UV filter, an inorganic particulate UV filter, or a combination thereof. Thus, "at least one particulate UV filter" may preferably refer to from 1 to 3 organic particulate UV filters, to 1 to 3 inorganic particulate UV filters, or to from 1 to 3 organic and inorganic particulate UV filters.

In one preferred embodiment, the at least one particulate UV filter is an organic particulate UV filter, or a combination of 2 or 3 organic particulate UV filters.

In another preferred embodiment, the at least one particulate UV filter is an inorganic particulate UV filter, or a combination of 2 or 3 organic particulate UV filters.

In another preferred embodiment, the at least one particulate UV filter is a combination of 2 or 3 inorganic and organic particulate UV filters.

In view of the fact that MBBT is also a particulate UV filter, it is to be understood that, if the sunscreen or daily care composition further comprises at least one particulate UV filter, said particulate UV filter is different from MBBT.

Similarly, in view of the fact that TBPT is also a particulate UV filter, it is to be understood that, if the sunscreen or daily care composition further comprises at least one particulate UV filter, said particulate UV filter is also different from TBPT.

In a preferred embodiment, the at least one organic particulate filter is selected from the group consisting of 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), and combinations thereof. In connection with the above preferred embodiment, it is to be understood that, if two organic particulate filters are present, also combinations of organic particulate filters are possible, e.g., the combination of bis-(diethylaminohydroxybenzoyl benzoyl) piperazine and phenylene bis-diphenyltriazine.

In a preferred embodiment, the at least one inorganic particulate UV filter is selected from the group consisting of titanium dioxide, zinc oxide, and combinations thereof.

In connection with the above preferred embodiment, it is to be understood that, if two inorganic particulate filters are present, the combination of titanium dioxide and zinc oxide is preferred.

If combinations of 2 or 3 inorganic and organic particulate UV filters are present, the following combinations are individually preferred:
bis-(diethylaminohydroxybenzoyl benzoyl) piperazine and titanium dioxide,
bis-(diethylaminohydroxybenzoyl benzoyl) piperazine and zinc oxide,
phenylene bis-diphenyltriazine and titanium dioxide,
phenylene bis-diphenyltriazine and zinc oxide,
bis-(diethylaminohydroxybenzoyl benzoyl) piperazine, titanium dioxide, and zinc oxide,
phenylene bis-diphenyltriazine, titanium dioxide, and zinc oxide, bis-(diethylaminohydroxybenzoyl benzoyl) piperazine, phenylene bis-diphenyltriazine, and titanium dioxide, bis-(diethylaminohydroxybenzoyl benzoyl) piperazine, phenylene bis-diphenyltriazine, zinc oxide.

In a preferred embodiment, the sunscreen or daily care composition comprises the at least one particulate UV filter in an amount of from 0.1 to 10% by weight, preferably in an amount of from 0.5 to 7% by weight, based on the total weight of the sunscreen or daily care composition. It is to be understood that these amounts refer to each individual particulate UV filter in the sunscreen or daily care composition. Thus, each individual particulate UV filter in the sunscreen or daily care composition is preferably present in an amount of from 0.1 to 10% by weight, preferably in an amount of from 0.5 to 7% by weight, based on the total weight of the sunscreen or daily care composition. If two or more particulate UV filters are present in the sunscreen or daily care composition, the overall amount of particulate UV filters may preferably be in the range of from 1 to 30% by weight, preferably from 2 to 30% by weight, based on the total weight of the sunscreen or daily care composition.

It is to be understood that the above amounts refer to the at least one particulate UV filter, which is present in the sunscreen or daily care composition in addition to the MBBT, and optionally TBPT, which are particulate UV filters themselves. As indicated above, the MBBT is preferably present in an amount of from 0.1 to 10% by weight, preferably in an amount of from 0.5 to 5% by weight, based on the total weight of the sunscreen composition.

As explained above, it can be preferred according to the present invention that the sunscreen or daily care composition comprises, apart from the methylene bis-benzotriazolyl tetramethylbutylphenol, and optionally TBPT, only at least one further particulate UV filter, but no further oil soluble or water soluble UV filter. The sunscreen or daily care composition is then exclusively based on particulate UV filters. Thus, in a preferred embodiment of the invention, the sunscreen or daily care composition comprises 2,2'-methylene bis[6-(2H-benzodiazol-2-yl)-4-(1,1,3,3-tetramethylbutyl)phenol] (INCI methylene bis-benzotriazolyl tetramethylbutylphenol), optionally in combination with 2,4,6-tris (biphenyl-4-yl)-1,3,5-triazine (INCI tris-biphenyl triazine), and at least one particulate UV filter, but no further oil soluble or water soluble UV filter. In connection with the at least one particulate UV filter being present in addition to methylene bis-benzotriazolyltetramethylbutylphenol, and optionally tris-biphenyl triazine, the above preferred embodiments regarding the particulate UV filters, in particular the inorganic and organic UV filters and any combinations thereof, are relevant. Preferably, at least two additional particulate UV filters are present in the sunscreen or daily care composition, as no further oil soluble or water soluble UV filter is present. Each individual particulate UV filter, which is present in the sunscreen or daily care composition in addition to methylene bis-benzotriazolyl tetramethylbutylphenol, and optionally tris-biphenyl triazine, is preferably present in an amount of from 0.1 to 10% by weight, preferably in an amount of from 0.5 to 7% by weight, based on the total weight of the sunscreen or daily care composition. In a preferred embodiment, the sunscreen or daily care composition comprises an overall amount of from 2 to 30% by weight of the sunscreen or daily care composition, of particulate UV filters, which are present in addition to methylene bis-benzotriazolyl tetramethylbutylphenol, and optionally tris-biphenyl triazine, if no further oil soluble or water soluble UV filters are present. As indicated above, the MBBT is preferably present in an amount of from 0.1 to 10% by weight, preferably in an amount of from 0.5 to 5% by weight, based on the total weight of the sunscreen composition.

In a preferred embodiment, the sunscreen or daily care composition comprises at least one oil soluble UV-A filter in an amount of at most 3% by weight, preferably in an amount of at most 2% by weight, based on the total weight of the sunscreen or daily care composition. The term "at least one oil soluble UV-A filter" may preferably refer to from 1 to 3 oil soluble UV-A filters, preferably to 1 or 2 oil soluble UV-A filters.

In a preferred embodiment, the at least one oil soluble UV-A filter is selected from the group consisting of hexyl 2-[4-(diethylamino)-2-hydroxybenzoyl]benzoate (INCI diethylamino hydroxybenzoyl hexyl benzoate), 1-(4-(1,1-dimethylethyl)phenyl)-3-(4-methoxyphenyl)propane-1,3-dione (INCI butyl methoxydibenzoylmethane), 2-(2H-benzotriazol-2-yl)-6-[(2-ethylhexyloxy)methyl]-4-methylphenol, 2-(2H-benzotriazol-2-yl)-4-methyl-6-[2-methyl-3-[1,3,3,3-tetramethyl-1-[(trimethylsilyl)oxy]-1-disiloxanyl]propyl]phenol (INCI drometrizole trisiloxane), and combinations thereof. Preferably, the oil soluble UV-A filter is hexyl 2-[4-(diethylamino)-2-hydroxybenzoyl]benzoate (INCI diethylamino hydroxybenzoyl hexyl benzoate) or 1-(4-(1,1-dimethylethyl)phenyl)-3-(4-methoxyphenyl)propane-1,3-dione (INCI butyl methoxydibenzoylmethane). In connection with the above preferred embodiments, it is to be understood that, if two oil soluble UV-A filters are present, also combinations of the above defined oil soluble UV-A filters are possible, e.g., the combinations of diethylamino hydroxybenzoyl hexyl benzoate and bis-ethylhexyloxyphenol methoxyphenyl triazine,
diethylamino hydroxybenzoyl hexyl benzoate and butyl methoxydibenzoylmethane,
diethylamino hydroxybenzoyl hexyl benzoate and drometrizole trisiloxane,
butyl methoxydibenzoylmethane and drometrizole trisiloxane.

Furthermore, if three oil soluble UV-A filters are present, the following combinations of oil soluble UV-A filters are preferred:

diethylamino hydroxybenzoyl hexyl benzoate, butyl methoxydibenzoylmethane, and drometrizole trisiloxane.

In a preferred embodiment, the sunscreen or daily care composition comprises the at least one oil soluble UV-A filter in an amount of at most 3% by weight, preferably in an amount of from 0.1 to 2% by weight, based on the total weight of the sunscreen or daily care composition. It is to be understood that these amounts refer to each individual oil soluble UV-A filter in the sunscreen or daily care composition. Thus, each individual oil soluble UV-A filter in the sunscreen or daily care composition is preferably present in an amount of at most 3% by weight, preferably in an amount of from 0.1 to 2% by weight, based on the total weight of the sunscreen or daily care composition. If two or more oil soluble UV-A filters are present in the sunscreen or daily care composition, the overall amount of oil soluble UV-A filters may preferably be in the range of from 0.1 to 3% by weight, preferably from 0.5 to 2.0% by weight, based on the total weight of the sunscreen or daily care composition.

As indicated above, the MBBT is preferably present in an amount of from 0.1 to 10% by weight, preferably in an amount of from 0.5 to 5% by weight, based on the total weight of the sunscreen composition.

As indicated above, it is to be understood that in certain preferred embodiments of the invention, the sunscreen or daily care composition may not only comprise MBBT, and optionally TBPT, and at least one oil soluble UV-A filter as defined above, but also at least one particulate UV filter as defined above, and/or at least one water soluble UV filter as defined hereinafter.

In a preferred embodiment, the sunscreen or daily care composition comprises at least one water soluble UV filter. The term "at least one water soluble UV filter" may preferably refer to from 1 to 3 water soluble UV filters, preferably to 1 or 2 water soluble UV filters.

In a preferred embodiment, the at least one water soluble UV filter is selected from the group consisting of R3Z)-3-[[4-[(Z)-[7,7-dimethyl-2-oxo-1-(sulfomethyl)-3-bicyclo[2.2.1]heptanylidene]methyl]phenyl]methylidene]-7,7-dimethyl-2-oxo-1-bicyclo[2.2.1]heptanyl]methanesulfonic acid (INCI terephthalylidene dicamphor sulfonic acid), 2-phenyl-1H-benzimidazole-5-sulfonic acid (INCI phenylbenzimidazole sulfonic acid), disodium phenyl dibenzimidazole tetrasulfonate, and combinations thereof. In connection with the above preferred embodiment, it is to be understood that, if two water soluble UV filters are present, also combinations of the above defined water soluble UV filters are possible, e.g., the combinations of
- terephthalylidene dicamphor sulfonic acid and phenylbenzimidazole sulfonic acid,
- terephthalylidene dicamphor sulfonic acid and disodium phenyl dibenzimidazole tetrasulfonate, or
- phenylbenzimidazole sulfonic acid and disodium phenyl dibenzimidazole tetrasulfonate.

Furthermore, if three water soluble UV filters are present, the combination of terephthalylidene dicamphor sulfonic acid, phenylbenzimidazole sulfonic acid, and disodium phenyl dibenzimidazole tetrasulfonate is preferred.

In a preferred embodiment, the sunscreen or daily care composition comprises the at least one water soluble UV filter in an amount of from 0.1 to 6% by weight, preferably in an amount of from 0.5 to 3% by weight, based on the total weight of the sunscreen or daily care composition. It is to be understood that these amounts refer to each individual water soluble UV filter in the sunscreen or daily care composition. Thus, each individual water soluble UV filter in the sunscreen or daily care composition is preferably present in an amount of from 0.1 to 6% by weight, preferably in an amount of from 0.5 to 3% by weight, based on the total weight of the sunscreen or daily care composition. If two or more water soluble UV filters are present in the sunscreen or daily care composition, the overall amount of water soluble UV filters may preferably be in the range of from 0.2 to 18% by weight, preferably from 0.5 to 12% by weight, more preferably from 1 to 10% by weight, based on the total weight of the sunscreen or daily care composition.

As indicated above, the MBBT is preferably present in an amount of from 0.1 to 10% by weight, preferably in an amount of from 0.5 to 5% by weight, based on the total weight of the sunscreen composition.

As indicated above, it is to be understood that in certain preferred embodiments of the invention, the sunscreen or daily care composition may not only comprise MBBT, and optionally TBPT, and at least one water soluble UV filter as defined above, but also at least one particulate UV filter as defined above, and/or at least one oil soluble UV-A filter as defined above.

In a preferred embodiment of the present invention, the sunscreen or daily care composition further comprises at least one UV-B filter, preferably at least one oil soluble UV-B filter.

In a preferred embodiment, the at least one further UV-B filter is selected from the group consisting of 4,4',4"-(1,3,5-triazine-2,4,6-triyltriimino)tris-benzoic acid-tris(2-ethylhexyl)ester (INCI ethylhexyl triazone), (RS)-2-ethylhexyl-2-hydroxybenzoate (INCI ethylhexyl salicylate), 3,3,5-trimethyl-cyclohexyl salicylate (homosalate), 2-ethylhexyl 2-cyano-3,3-diphenyl-2-propenoate (INCI octocrylene), (RS)-2-ethylhexyl-(2E)-3-(4-methoxyphenyl)prop-2-enoate (INCI ethylhexyl methoxycinnamate), malonate derivatives such as dimethicone diethyl benzalmalonate, diethylhexyl butamido triazone, and combinations thereof. In connection with the above preferred embodiment, it is to be understood that, if two further UV-B filters are present, also combinations of the above defined UV-B filters are possible. A preferred combination is the combination of ethylhexyl triazone and ethyl salicylate.

In a preferred embodiment, the sunscreen or daily care composition comprises the at least one further UV-B filter in an amount of from 0.1 to 10% by weight, based on the total weight of the sunscreen or daily care composition. It is to be understood that these amounts refer to each individual further UV-B filter in the sunscreen or daily care composition. Thus, each individual further UV-B filter in the sunscreen or daily care composition is preferably present in an amount of from 0.1 to 10% by weight, based on the total weight of the sunscreen or daily care composition. If two or more further UV-B filters are present in the sunscreen or daily care composition, the overall amount of further UV-B filters may preferably be in the range of from 0.2 to 20% by weight, preferably from 1 to 12% by weight, more preferably from 1 to 10% by weight, based on the total weight of the sunscreen or daily care composition.

In a preferred embodiment of the invention, the sunscreen or daily care composition further comprises at least one oil soluble broad spectrum UV filter, wherein the at least one oil soluble broad spectrum UV filer is preferably 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine).

In a preferred embodiment, the sunscreen or daily care composition comprises the bis-ethylhexyloxyphenol methoxyphenyl triazine (BEMT) in an amount of at most 3% by weight, preferably in an amount of at most 2% by weight, based on the total weight of the sunscreen or daily care composition.

In certain preferred embodiments of the invention, the sunscreen or daily care composition comprises in addition to MBBT optionally the particulate UV filter tris-biphenyl triazine, also referred to as TBPT, and at least one of the following UV filters:
- the oil soluble UV-A filter diethylamino hydroxybenzoyl hexyl benzoate, also referred to as DHHB, or butyl methoxydibenzoylmethane, also referred to as BMDBM, or
- the inorganic particulate UV filter $TiO_2$, and optionally
- at least one of the UV-B filters ethylhexyl triazone, also referred to as EHT, or ethyl salicylate, also referred to as EHS, or diethylhexylbutamido triazone, also referred to as DBT, and optionally
- the oil soluble broad spectrum UV filter bis-ethylhexyloxyphenol methoxyphenyl triazine, also referred to as BEMT.

Preferred UV filter combinations of the present application, e.g. include MBBT+TBPT+EHT+EHS or MBBT+TBPT+DHHB+EHT+EHS or MBBT+TBPT+$TiO_2$. Further preferred UV filter combinations include MBBT+DBT+ BEMT or MBBT+DHHB+BEMT or MBBT+BMDBM+ BEMT.

In particular, the following sunscreen copositions are preferred according to the present invention and in connection with the above defined uses and methods:

In one embodiment, the present invention relates to a sunscreen composition comprising 2,2'-methylene bis[6-(2H-benzotriazol-2-yl)-4-(1,1,3,3-tetramethylbutyl)phenol] (INCI methylene bis-benzotriazolyl tetramethylbutylphenol), i.e. MBBT, and (a1) at least one oil soluble UV-A filter, wherein the at least one oil soluble UV-A filter is present in an amount of at most 3% by weight, based on the total weight of the sunscreen or daily care composition, and wherein the at least one oil soluble UV-A filter is hexyl 2-[4-(diethylamino)-2-hydroxybenzoyl]benzoate (INCI diethylamino hydroxybenzoyl hexyl benzoate), i.e. DHHB, or 1-(4-(1,1-dimethylethyl)phenyl)-3-(4-methoxyphenyl)propane-1,3-dione (INCI butyl methoxydibenzoylmethane), i.e. BMDBM or (a2) at least one UV-B filter, which is diethylhexyl butamido triazone, i.e. DBT; and (b) at least one oil soluble broad spectrum UV filter, wherein the at least one oil soluble broad spectrum UV filer is preferably 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine), i.e. BEMT.

In other words, the present invention relates to the use of 2,2'-methylene bis[6-(2H-benzotriazol-2-yl)-4-(1,1,3,3-tetramethylbutyl)phenol] (INCI methylene bis-benzotriazolyl tetramethylbutylphenol), to reduce fabric staining of a sunscreen or daily care composition and/or to facilitate the washability of a sunscreen or daily care composition from textiles, wherein the sunscreen or daily care composition further comprises (a1) at least one oil soluble UV-A filter, wherein the at least one oil soluble UV-A filter is present in an amount of at most 3% by weight, based on the total weight of the sunscreen or daily care composition, and wherein the at least one oil soluble UV-A filter is hexyl 2-[4-(diethylamino)-2-hydroxybenzoyl]benzoate (INCI diethylamino hydroxybenzoyl hexyl benzoate), i.e. DHHB, or 1-(4-(1,1-dimethylethyl)phenyl)-3-(4-methoxyphenyl)propane-1,3-dione (INCI butyl methoxydibenzoylmethane), i.e. BMDBM or (a2) at least one UV-B filter, which is diethylhexyl butamido triazone, i.e. DBT; and (b) at least one oil soluble broad spectrum UV filter, wherein the at least one oil soluble broad spectrum UV filer is preferably 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine), i.e. BEMT.

The sunscreen composition may optionally comprise further UV filters as defined above.

In one preferred embodiment, the present invention relates to a sunscreen composition comprising at least
MBBT,
DHHB and/or BMDBM, and
BEMT.

The sunscreen composition may optionally comprise further UV filters as defined above. For example, optionally, TBPT and/or at least one UV-B filter selected from EHT, EHS, and DBT may additionally be present.

In another preferred embodiment, the present invention relates to a sunscreen composition comprising at least
MBBT,
BEMT, and
DBT.

The sunscreen composition may optionally comprise further UV filters as defined above. For example, optionally, TBPT and/or at least one UV-B filter selected from EHT and EHS may additionally be present. Alternatively or additionally, at least one UV-A filter selected from DHHB and BMDBM may optionally be present. 2,4,6-Tris(biphenyl-4-yl)-1,3,5-triazine (INCI tris-biphenyl triazine), also referred to as TBPT, is a particulate organic UV filter belonging to the group of triazine derivatives. It is sold under the tradename Tinosorb A2B by BASF. It is a broad spectrum UV filter providing protection in the UV-A and UV-B range.

Hexyl 2-[4-(diethylamino)-2-hydroxybenzoyl]benzoate (INCI diethylamino hydroxybenzoyl hexyl benzoate), also referred to as DHHB, is an UV filter belonging to the group of benzophenone derivatives. It is sold under the tradename Uvinul A Plus by BASF. It is an UV-A filter.

1-(4-(1,1-dimethylethyl)phenyl)-3-(4-methoxyphenyl) propane-1,3-dione (INCI butyl methoxydibenzoylmethane), also referred to as BMDBM, is a diketone UV filter. It is an UV-A filter.

4,4',4"-(1,3,5-Triazin-2,4,6-triyltriimino)tris-benzoic acid-tris(2-ethylhexyl)ester (INCI ethylhexyl triazone), also referred to as EHT, is an UV filter belonging to the group of triazine derivatives. It is sold under the tradename Uvinul T150 by BASF. It is an UV-B filter.

Diethylhexyl butamido triazone, also referred to as DBT, is an UV-B filter.

(RS)-2-Ethylhexyl-2-hydroxybenzoate (INCI ethylhexyl salicylate), also referred to as EHS, is an UV filter belonging to the group of salicylic derivatives. It is, e.g., sold under the tradename Neo Heliopan OS by Symrise. It is an UV-B filter.

2,4-Bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine), also referred to as BEMT is an UV filter belonging to the group of triazine derivatives. It is sold under the tradename Tinosorb S by BASF. It is a broad spectrum UV filter.

In connection with the above preferred embodiments, it is to be understood that the total weight of the sunscreen or daily care composition refers to the sunscreen or daily care composition as defined above, wherein the sunscreen composition may comprise at least one additive.

In one embodiment, the at least one additive is selected from the group consisting of emulsifier, emollients, viscosity regulators (thickeners), sensory enhancers, adjuvants, preservatives, and combinations thereof.

Preferred emulsifiers include
glucose derivatives such as cetearyl glucoside, arachidyl glucoside, lauryl glucoside, polyglyceryl-3 methylglucose distearate, methyl glucose sesquistearate;
sucrose derivative such as sucrose polystearate, sucrose palmitate;
sorbitol derivatives such as polysorbate-n, PEG-10 sorbitan laurate;
fatty alcohol polyglycolethers and fatty acid polyglycolethers such as ceteareth-20, beheneth-25, steareth-2, PEG-100 stearate;
glycerides of fatty acids such as glyceryl stearate, glyceryl oleate;
glumatic acid derivatives such as sodium stearoyl glutamate;

sulfosuccinic acid derivatives such as disodium Cetearyl sulfosuccinate;

phosphoric acid derivatives such as potassium cetyl phosphate;

fatty acid esters of polyglyceryl such as polyglyceryl-3-diisostearate, polyglyceryl-2-dipolyhydroxystearate;

oxyalkenylated organomodified silicone/polysiloxane/polyalkyl/polyether copolymers and derivatives.

Preferred emollients include esters of linear or branched fatty acids with linear or branched fatty alcohols such as propylheptyl caprylate, coco caprylate, isopropyl myristate, ethylhexyl palmitate;

esters of aromatic carboxylic acids with linear or branched fatty alcohols such as $C_{12}$-$C_{15}$-alkyl benzoate, ethylhexyl benzoate, phenethyl benzoate;

dicarboxylic acid esters with linear or branched alcohols such as dibutyl adipate, dicaprylyl carbonate, diisopropyl sebacate;

esters of hydroxycarboxylic acids with linear or branched fatty alcohols;

esters of linear or branched fatty acids with polyhydric alcohol such as butylene glycol dicaprylate/dicaprate;

mono-, di-, tri-glycerides based on $C_6$-$C_{18}$ fatty acids such as caprylic/capric triglycerides, coco glycerides;

guerbet alcohols such as octyldodecynol;

hydrocarbons such as hydrogenated polyisobutene, mineral oil, squalene, isohexadecane;

ethers such as dicaprylyl ether;

silicone derivatives (organomodified polysiloxanes) such as dimethylpolysiloxane, cyclic silicones.

Preferred thickeners include fatty alcohols such as cetyl alcohol, cetearyl alcohol, stearyl alcohol;

fatty acids such as stearic acid;

fatty acid esters such as myristyl stearate;

waxes such as beeswax, carnauba wax, microcrystalline wax, ceresin, ozocerite;

polysaccharides or derivatives such as xanthan gum, guar gum, agar gum, alginates, gellan gum, carraghenan;

polyacrylates or homopolymers of reticulated acrylic acids or polyacrylamides such as carbomers, acrylate copolymers, acrylate/$C_{10}$-$C_{30}$-alkyl acrylate crosspolymer, acrylate/beheneth-25 methacrylate copolymer;

silicate derivatives such as magnesium silicates;

cellulose derivatives such as hydroxypropyl cellulose.

Preferred sensory enhancers include polyamide derivatives such as nylon-12;

polymethyl methacrylates;

silica;

mica;

polymethylsilsesquioxane;

polyethylene;

starch derivatives such as aluminum starch octenylsuccinate;

dimethicone derivatives;

boron nitride;

HDI/trimethylol hexyllactone crosspolymer.

Preferred adjuvants include tocopherol derivatives;

retinol derivatives;

ascorbic acid derivatives;

bisabolol;

allantoin;

panthenol;

chelating agents (EDTA, EDDS, EGTA, phytic acid, piroctone olamine);

ethylhexyl glycerin;

caprylyl glycol;

hydroxyacetophenone;

caprylhydroxymic acid;

propellants such as propane, butane, isobutene, dimethyl ether;

styrene/PVP or styrene acrylamide copolymers;

insect repellants such as butylacetylaminopropionate.

Preferred preservatives include paraben derivatives;

benzyl alcohol;

phenoxyethanol;

zingerone.

In connection with the above preferred embodiments, it is to be understood that if the sunscreen or daily care composition comprises two or more additives, combinations of the additives as defined above are also part of the invention.

In connection with the above preferred and particularly preferred embodiments, it is to be understood that the sunscreen or daily care composition may further comprise water. In case water is present in the sunscreen composition, the sunscreen composition can be an oil in water emulsion (O/W emulsion) or a water in oil emulsion (W/O emulsion).

The present invention is further illustrated by the following examples.

EXAMPLES

Process of Manufacture of Sunscreen Compositions

The ingredients of part A as well as the ingredients of part B as provided in Tables 1.1, 1.2, 1.3, and 1.4 below for each tested sunscreen composition were combined and heated to 80° C., wherein part A was added to part B under stirring and was further homogenized. Subsequently, the composition was cooled down to room temperature under stirring. Then, part C and part D were added at room temperature.

Sunscreen Compositions

The sunscreen compositions compared with each other in each case provide comparable UV-A and SPF protection.

TABLE 1.1

| Ingredient (Trade Name) | Composition 1a | Comparative Composition 1b |
|---|---|---|
| Part A | | |
| Sucrose Polystearate, Hydrogenated Polyisobutene (Emulgade Sucro plus) | 3.00 | 3.00 |
| Disodium Cetearyl Sulfosuccinate (Eumulgin Prisma) | 1.00 | 1.00 |
| Cetearyl Alcohol (Lanette O) | 2.00 | 2.00 |
| Propylheptyl Caprylate (Cetiol Sensoft) | 5.00 | 5.00 |
| Dicaprylyl Carbonate (Cetiol CC) | 5.00 | 5.00 |
| Dibutyl Adipate (Cetiol B) | 5.00 | 5.00 |
| Phenoxyethanol and Ethylhexylglycerin (Euxyl PE 9010) | 1.00 | 1.00 |
| EHT (Uvinul T150) | 2.00 | 2.00 |
| EHS (Neo Heliopan OS) | 5.00 | 5.00 |
| BEMT (Tinosorb S) | — | 2.00 |
| Part B | | |
| Water | Qsp 100 | Qsp 100 |
| Glycerine | 6.00 | 6.00 |
| Xanthan Gum (Rheocare XGN) | 0.20 | 0.20 |

TABLE 1.1-continued

| Ingredient (Trade Name) | Composition 1a | Comparative Composition 1b |
|---|---|---|
| Part C | | |
| MBBT in the form of a dispersion of 50% by weight MBBT in water (Tinosorb M) | 7.00 | — |
| TBPT in the form of a dispersion of 50% by weight TBPT in water (Tinosorb A2B) | 4.00 | 4.00 |
| Part D | | |
| Undecane, Tridecane (Cetiol Ultimate) | 3.00 | 3.00 |
| Total | 100.00 | 100.00 |

TABLE 1.2

| Ingredient (Trade Name) | Composition 2a | Composition 2b | Comparative Composition 2c |
|---|---|---|---|
| Part A | | | |
| Sucrose Polystearate, Hydroenated Polyisobutene (Emulgade Sucro plus) | 3.00 | 3.00 | 3.00 |
| Disodium Cetearyl Sulfosuccinate (Eumulgin Prisma) | 1.00 | 1.00 | 3.00 |
| Cetearyl Alcohol (Lanette O) | 2.00 | 2.00 | 1.00 |
| Propylheptyl Caprylate (Cetiol Sensoft) | 5.00 | 5.00 | 5.00 |
| Cetiol OE | | | 3.00 |
| Dicaprylyl Carbonate (Cetiol CC) | 5.00 | 5.00 | |
| Dibutyl Adipate (Cetiol B) | 5.00 | 5.00 | 10.00 |
| Phenoxyethanol and Ethylhexylglycerin (Euxyl PE 9010) | 1.00 | 1.00 | 1.00 |
| EHT (Uvinul T150) | 2.00 | 2.00 | 1.50 |
| EHS (Neo Heliopan OS) | 5.00 | 5.00 | 5.00 |
| DHHB (Uvinul A Plus) | 2.00 | 3.00 | 3.00 |
| BEMT (Tinosorb S) | — | — | 1.00 |
| Part B | | | |
| Water | Qsp 100 | Qsp 100 | Gsp 100 |
| Glycerine | 6.00 | 6.00 | 2.00 |
| Xanthan Gum (Rheocare XGN) | 0.20 | 0.20 | 0.20 |
| Part C | | | |
| MBBT in the form of a dispersion of 50% by weight MBBT in water (Tinosorb M) | 6.00 | 6.00 | — |
| TBPT in the form of a dispersion of 50% by weight TBPT in water (Tinosorb A2B) | 2.00 | 2.00 | 4.40 |
| Part D | | | |
| Undecane, Tridecane (Cetiol Ultimate) | 3.00 | 3.00 | 2.00 |
| Total | 100.00 | 100.00 | 100.00 |

TABLE 1.3

| Ingredient (Trade Name) | Composition 3a | Comparative Composition 3b |
|---|---|---|
| Part A | | |
| Sucrose Polystearate, Hydrogenated Polyisobutene (Emulgade Sucro plus) | 3.00 | 3.00 |
| Disodium Cetearyl Sulfosuccinate (Eumulgin Prisma) | 1.00 | 1.00 |
| Cetearyl Alcohol (Lanette O) | 2.00 | 2.00 |
| Propylheptyl Caprylate (Cetiol Sensoft) | 5.00 | 5.00 |
| Dicaprylyl Carbonate (Cetiol CC) | 5.00 | 5.00 |
| Dibutyl Adipate (Cetiol B) | 5.00 | 5.00 |
| Phenoxyethanol and Ethylhexylglycerin (Euxyl PE 9010) | 1.00 | 1.00 |
| EHT (Uvinul T150) | — | 2.00 |
| EHS (Neo Heliopan OS) | — | 5.00 |
| DHHB (Uvinul A Plus) | — | 5.00 |
| BEMT (Tinosorb S) | — | 1.50 |
| $TiO_2$ powder comprising 80% by weight of $TiO_2$ and 20% by weight coating material comprising $Al(OH)_3$ and Stearic Acid (MT-100Z) | 3.15 | — |
| Part B | | |
| Water | Qsp 100 | Qsp 100 |
| Glycerine | 6.00 | 6.00 |
| Xanthan Gum (Rheocare XGN) | 0.20 | 0.20 |
| Part C | | |
| Phenylbenzimidazol sulfonic acid (Eusolex 232) | — | 2.00 |
| 2-Amino-2-hydroxymethyl-1,3-propanediol (Tris-amino) | — | 0.90 |
| Water | — | 10.00 |
| MBBT in the form of a dispersion of 50% by weight MBBT in water (Tinosorb M) | 9.00 | — |
| TBPT in the form of a dispersion of 50% by weight TBPT in water (Tinosorb A2B) | 8.00 | — |
| Part D | | |
| Undecane, Tridecane (Cetiol Ultimate) | 3.00 | 3.00 |
| Total | 100.00 | 100.00 |

TABLE 1.4

| Ingredient (Trade Name) | Comparative Composition 4a | Composition 4b | Composition 4c |
|---|---|---|---|
| Part A | | | |
| Glyceryl Stearate (Cutina GMS V) | 1.00 | 1.00 | 1.00 |
| Sodium Stearyl Glutamate (Emulgin ® SG) | 0.30 | 0.30 | 0.30 |
| Stearyl Alcohol (Lanette 18) | 1.00 | 1.00 | 1.00 |
| Butylene Glycol Dicaprylate/Dicaprate (Dermofeel BCG) | 4.00 | 4.00 | 4.00 |
| Dibutyl Adipate (Cetiol B) | 3.00 | 3.00 | 3.00 |
| C12-15 Alkyl Benzoate (Cetiol AB) | 5.00 | 5.00 | 5.00 |
| Phenoxyethanol (Protectol PE) | 1.00 | 1.00 | 1.00 |
| VP/Hexadecene Copolymer (Antaron VP216) | 0.50 | 0.50 | 0.50 |
| Silica Dimethyl Silylate (Aerosil R972) | 1.00 | 1.00 | 1.00 |
| BMDBM (Parsol 1789) | 4.75 | 4.75 | 4.75 |
| EHS (Neoheliopan OS) | 4.75 | 4.75 | 4.75 |
| EHT (Uvinul T150) | 3.00 | 3.00 | 3.00 |
| BEMT (Tinosorb S) | 4.00 | 4.00 | 4.00 |
| DHHB (Uvinul A Plus) | 1.00 | 0.25 | — |

TABLE 1.4-continued

| Ingredient (Trade Name) | Comparative Composition 4a | Composition 4b | Composition 4c |
|---|---|---|---|
| Part B | | | |
| Water | Qsp 100% | Qsp 100% | Qsp 100% |
| Glycerin | 7.50 | 7.50 | 7.50 |
| Acrylates/C10-30 Alkyl Acrylate Crosspolymer (Pemulen TR2) | 0.10 | 0.10 | 0.10 |
| Xanthan Gum (Rheocare XGN) | 0.40 | 0.40 | 0.40 |
| Disodium EDTA (EDTA BD) | 0.20 | 0.20 | 0.20 |
| Part C | | | |
| PBSA (Eusolex 232) | 1.00 | 1.00 | 1.00 |
| Water | 5.00 | 5.00 | 5.00 |
| NaOH 30% | 0.25 | 0.30 | 0.22 |
| Part D | | | |
| MBBT* nano, Aqua, Decyl Glucoside (Tinosorb M) | — | 1.50 | 2.00 |
| Ethanol | 3.00 | 3.00 | 3.00 |
| Total | 100.00 | 100.00 | 100.00 |
| SPF** | 35.9 | 37.8 | 38.5 |
| UVA-PF** (using a SPF of 30) | 12.2 | 12.6 | 12.6 |

*Tinosorb M is a 50% active dispersion, i.e. 2% Tinosorb M correspond to 1% active UV filter amount.
**calculated values.

Measurement of Fabric Staining

Fabric staining of sunscreen compositions was measured by the L*a*b method as described above. The measurement was performed with a spectrophotometer using the following instrument: Remission Spectrometer Datacolor SF 400 (light D65, observer 10°).

The difference between the color of a sunscreen composition stain on a white textile and the color of the white textile alone was determined following the assumption that $\Delta E^* = \Delta b^*$ in order to determine fabric staining. The lower the color difference, the lower is the fabric staining.

Further, the difference between the color of a sunscreen composition stain on a white textile after 1 or 3 washing cycles and the color of the white textile alone was determined following the assumption that $\Delta E^* = \Delta b^*$ in order to determine the washability. The lower the color difference in comparison to the value obtained before washing, the more has fabric staining been reduced, i.e. the better the washability of the sunscreen composition from textiles.

For applying the sunscreen compositions in order to make a stain on a white textile, the sunscreen composition was diluted in water or ethanol at a concentration of 10% by weight based on the total weight of the diluted mixture. 300 mg (15 mg/cm$^2$) of the diluted mixture was applied on a white textile (whiteness adjusted to: WG 170±10, after washing WG 190±10) in order to obtain a stain.

For determining the washability, 1 or 3 washing cycles were performed in a washing machine using a temperature of 40° C. for 20 minutes and Persil Universal Gel obtained from Henkel (3 g on stain). Each textile was washed separately.

Figure 1:
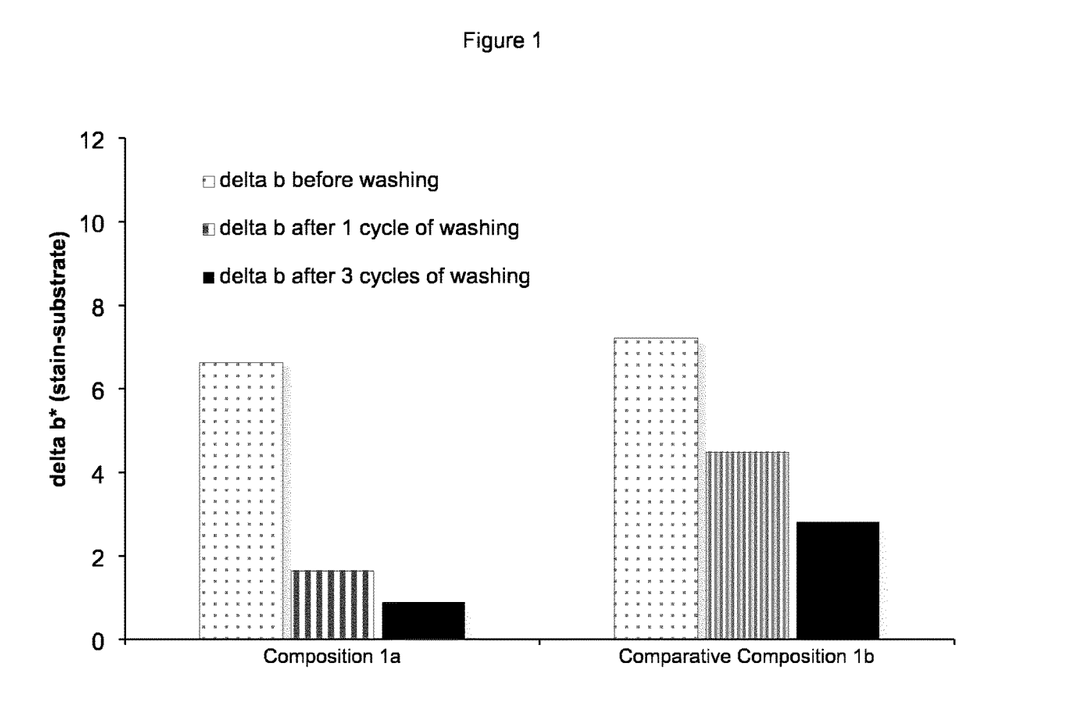
Figure 2:
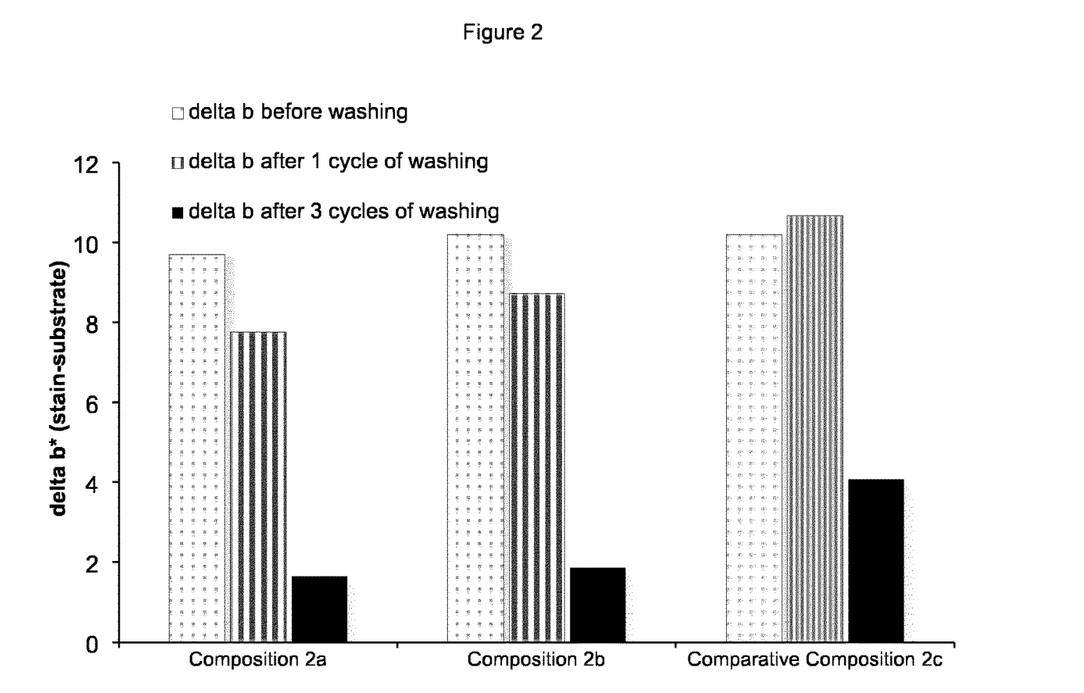
Figure 3:
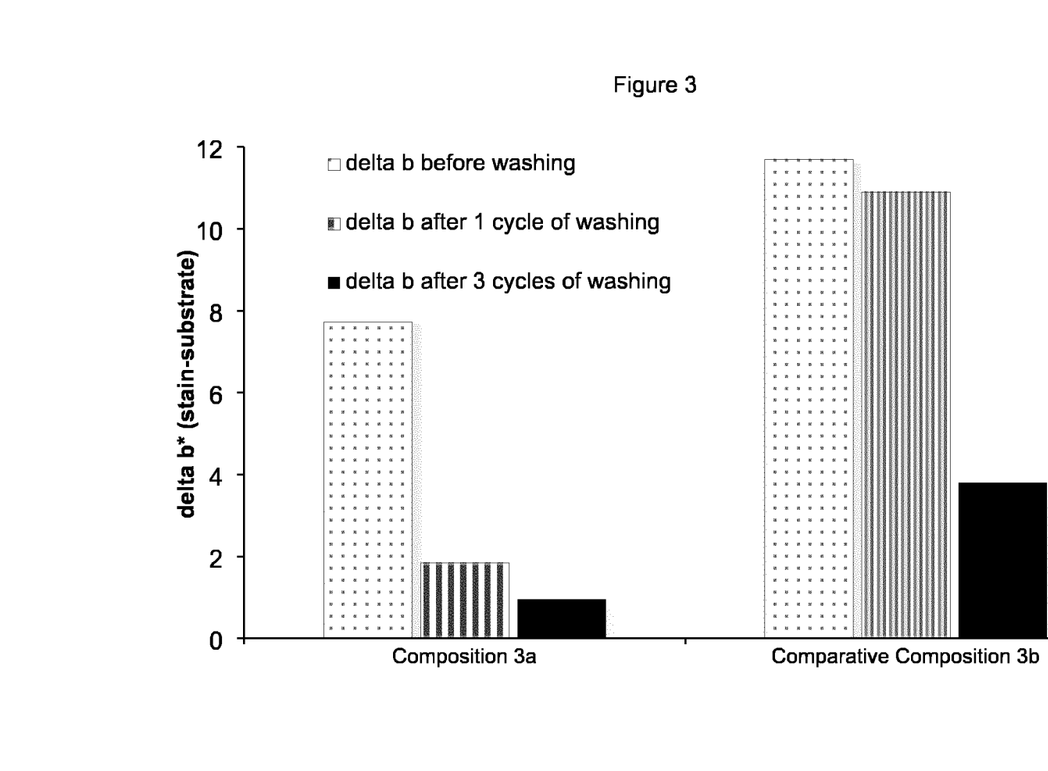

The results of sunscreen compositions 1a, 1b, 2a, 2b, 2c, 3a, 3b, 4a, 4b and 4c are shown in Tables 2.1, 2.2, 2.3, and 2.4 as well as in FIGS. 1, 2, 3, and 4.

BRIEF DESCRIPTION OF THE DRAWINGS

FIG. 1, FIG. 2, FIG. 3, and FIG. 4 show the results of sunscreen compositions 1a, 1b, 2a, 2b, 2c, 3a, 3b, 4a, 4b, and 4c.

TABLE 2.1

| | Composition 1a | Comparative Composition 1b |
|---|---|---|
| Δb* (before washing) | 6.63 | 7.22 |
| SD (before washing) | 0.11 | 0.16 |
| Δb* (after 1 cycle) | 1.65 | 4.49 |
| SD (after 1 cycle) | 0.11 | 0.06 |
| Δb* (after 3 cycles) | 0.89 | 2.82 |
| SD (after 3 cycles) | 0.07 | 0 |

TABLE 2.2

| | Composition 2a | Composition 2b | Comparative Composition 2c |
|---|---|---|---|
| Δb* (before washing) | 9.71 | 10.21 | 10.21 |
| SD (before washing) | 0.21 | 0.03 | 0.06 |
| Δb* (after 1 cycle) | 7.76 | 8.73 | 10.68 |
| SD (after 1 cycle) | 0.11 | 0.18 | 0.04 |
| Δb* (after 3 cycles) | 1.64 | 1.86 | 4.08 |
| SD (after 3 cycles) | 0.13 | 0.08 | 0.25 |

TABLE 2.3

| | Composition 3a | Comparative Composition 3b |
|---|---|---|
| Δb* (before washing) | 7.73 | 11.7 |
| SD (before washing) | 0.08 | 0.16 |
| Δb* (after 1 cycle) | 1.85 | 10.91 |
| SD (after 1 cycle) | 0.16 | 0.42 |
| Δb* (after 3 cycles) | 0.96 | 3.8 |
| SD (after 3 cycles) | 0 | 0.03 |

TABLE 2.4

| | Comparative Composition 4a | Composition 4b | Composition 4c |
|---|---|---|---|
| Δb* (before washing) | 10.99 | 10.38 | 10.50 |
| SD (before washing) | 0.26 | 0.12 | 0.05 |
| Δb* (after 1 cycle) | 8.54 | 7.73 | 7.89 |
| SD (after 1 cycle) | 0.25 | 0.27 | 0.28 |
| Δb* (after 3 cycles) | 5.38 | 4.75 | 4.91 |
| SD (after 3 cycles) | 0.33 | 0.12 | 0.07 |

The invention claimed is:

1. A method for reducing fabric staining of a sunscreen or daily care composition comprising incorporating 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine) into the sunscreen or daily care composition, wherein the sunscreen or daily care composition further comprises
   (i) at least one particulate UV-filter; and/or
   (ii) at least one oil soluble UV-A filter, wherein the at least one oil soluble UV-A filter is present in an amount of at most 3% by weight, based on the total weight of the sunscreen or daily care composition; and/or
   (iii) at least one water soluble UV filter.

2. A method for facilitating washability of a sunscreen or daily care composition from textiles, comprising incorporating 2,2'-methylene bis[6-(2H-benzotriazol-2-yl)-4-(1,1,3,3-tetramethylbutyl)phenol] (INCI methylene bis-benzotriazolyl tetramethylbutylphenol), optionally 2,4,6-tris(biphenyl- 4-yl)-1,3,5-triazine (INCI tris-biphenyl triazine), into the sunscreen or daily care composition, wherein the sunscreen or daily care composition further comprises
- (i) at least one particulate UV filter; and/or
- (ii) at least one oil soluble UV-A filter, wherein the at least one oil soluble UV-A filter is present in an amount of at most 3% by weight, based on the total weight of the sunscreen or daily care composition; and/or
- (iii) at least one water soluble UV filter.

3. The method according to claim 1, wherein the at least one particulate UV filter is an organic particulate UV filter, an inorganic particulate UV filter, or a combination thereof.

4. The method according to claim 1, wherein the at least one organic particulate UV-filter is selected from the group consisting of 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5', 6'-tetraphenyl-3-3'-(1,4-phenylene)bis(1,2,4-triazine) (INCI phenylene bis-diphenyltriazine), and combinations thereof.

5. The method according to claim 1, wherein the at least one inorganic particulate UV-filter is selected from the group consisting of titanium dioxide, zinc oxide, and combinations thereof.

6. The method according to claim 1, wherein the sunscreen or daily care composition comprises the at least one particulate UV filter in an amount of from 0.1 to 10% by weight, based on the total weight of the sunscreen or daily care composition.

7. The method according to claim 1, wherein the sunscreen or daily care composition comprises 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), and at least one further particulate UV filter, but no further oil soluble or water soluble UV filter.

8. The method according to claim 7, wherein the sunscreen or daily care composition comprises an overall amount of from 2 to 30% by weight, based on the total weight of the sunscreen or daily care composition, of particulate UV filters.

9. The method according to claim 1, wherein the at least one oil soluble UV-A filter is selected from the group consisting of hexyl 2-[4-(diethylamino)-2-hydroxybenzoyl]benzoate (INCI diethylamino hydroxybenzoyl hexyl benzoate), 1-(4-(1,1-dimethylethyl)phenyl)-3-(4-methoxyphenyl)propane-1,3-dione (INCI butyl methoxydibenzoylmethane), 2-(2H-benzotriazol-2-yl)-6-[(2-ethylhexyloxy)methyl]-4-methylphenol, 2-(2H-benzotriazol-2-yl)-4-methyl-6-[2-methyl-3-[1,3,3,3-tetramethyl-1-[(trimethylsilyl)oxy]-1-disiloxanyl]propyl]phenol (INCI drometrizole trisiloxane), and combinations thereof.

10. The method according to claim 1, wherein the at least one water soluble UV filter is selected from the group consisting of [(3Z)-3-[[4-[(Z)-[7,7-dimethyl-2-oxo-1-(sulfomethyl)-3-bicyclo[2.2.1]heptanylidene]methyl]phenyl]methylidene]-7,7-dimethyl-2-oxo-1-bicyclo[2.2.1]heptanyl]methanesulfonic acid (INCI terephthalylidene dicamphor sulfonic acid), 2-phenyl-1H-benzimidazole-5-sulfonic acid (INCI phenylbenzimidazole sulfonic acid), disodium phenyl dibenzimidazole tetrasulfonate, and combinations thereof.

11. The method according to claim 1, wherein the sunscreen or daily care composition comprises the at least one water soluble UV filter in an amount of from 0.1 to 6% by weight, based on the total weight of the sunscreen or daily care composition.

12. The method according to claim 1, wherein the sunscreen or daily care composition comprises the 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 0.1 to 10% by weight, based on the total weight of the sunscreen or daily care composition, and wherein the sunscreen or daily care composition optionally comprises the 2,4,6-tris(biphenyl-4-yl)-1,3,5-triazine (INCI tris-biphenyl triazine), if present, in an amount of from 0.1 to 10% by weight, based on the total weight of the sunscreen composition or daily care composition.

13. The method according to claim 1, wherein the sunscreen or daily care composition further comprises at least one UV-B filter, wherein the at least one further UV-B filter is selected from the group consisting of 4,4',4"-(1,3,5-triazine-2,4,6-triyltriimino)tris-benzoic acid-tris(2-ethylhexyl)ester (INCI ethylhexyl triazone), (RS)-2-ethylhexyl-2-hydroxybenzoate (INCI ethylhexyl salicylate), 3,3,5-trimethyl-cyclohexyl salicylate (homosalate), 2-ethylhexyl 2-cyano-3,3-diphenyl-2-propenoate (INCI octocrylene), (RS)-2-ethylhexyl-(2E)-3-(4-methoxyphenyl)prop-2-enoate (INCI ethylhexyl methoxycinnamate), malonate derivatives such as dimethicone diethyl benzalmalonate, diethylhexyl butamido triazone, and combinations thereof.

14. The method according to claim 1, wherein the sunscreen or daily care composition further comprises at least one oil soluble broad spectrum UV filter, wherein the at least one oil soluble broad spectrum UV filer is 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine).

15. A method for reducing fabric staining of a sunscreen or daily care composition and/or facilitating washability of the sunscreen or daily care composition from textiles, comprising incorporating 2,2'-methylene bis[6-(2H-benzotriazol-2-yl)-4-(1,1,3,3-tetramethylbutyl)phenol] (INCI methylene bis-benzotriazolyl tetramethylbutylphenol), optionally in combination with 2,4,6-tris(biphenyl-4-yl)-1,3,5-triazine (INCI tris-biphenyl triazine), into the sunscreen or daily care composition, wherein the sunscreen or daily care composition further comprises
- at least one UV-B filter, which is diethylhexyl butamido triazone; and
- at least one oil soluble broad spectrum UV filter, which is 2,4-bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine).

16. The method according to claim 1, wherein the sunscreen or daily care composition comprises the at least one particulate UV filter in an amount of from 0.5 to 7% by weight, based on the total weight of the sunscreen or daily care composition.

17. The method according to claim 7, wherein the sunscreen or daily care composition comprises an overall amount of from 5 to 20% by weight, based on the total weight of the sunscreen or daily care composition, of particulate UV filters.

18. The method according to claim 1, wherein the at least one oil soluble UV-A filter is hexyl 2-[4-(diethylamino)-2-hydroxybenzoyl]benzoate (INCI diethylamino hydroxybenzoyl hexyl benzoate) or 1-(4-(1,1-dimethylethyl)phenyl)-3-(4-methoxyphenyl)propane-1,3-dione (INCI butyl methoxydibenzoylmethane).

19. The method according to claim 1, wherein the sunscreen or daily care composition comprises the at least one water soluble UV filter in an amount of from 0.5 to 3% by weight, based on the total weight of the sunscreen or daily care composition.

20. The method according to claim 1, wherein the sunscreen or daily care composition comprises the 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 0.5 to 5% by weight, based on the total weight of the sunscreen or daily care composition, and wherein the sunscreen or daily care composition optionally comprises the 2,4,6-tris(biphenyl-4-yl)-1,3,5-triazine (INCI tris-biphenyl triazine), if present, in an amount of from 0.5 to 7% by weight, based on the total weight of the sunscreen composition or daily care composition.

* * * * *